US009528930B2

(12) United States Patent
Ishikawa et al.

(10) Patent No.: US 9,528,930 B2
(45) Date of Patent: Dec. 27, 2016

(54) ADHERING MATTER DETERMINATION DEVICE (71) Applicant: DENSO CORPORATION, Kariya, Aichi-pref. (JP)

(72) Inventors: Junichi Ishikawa, Kariya (JP); Jun Tarui, Kariya (JP); Kiyoshi Otsuka, Ichinomiya (JP); Makiko Sugiura, Hekinan (JP); Takahiko Yoshida, Okazaki (JP); Tomohide Ariki, Anjo (JP)

(73) Assignee: DENSO CORPORATION, Kariya (JP)

( * ) Notice: Subject to any disclaimer, the term of this patent is extended or adjusted under 35 U.S.C. 154(b) by 25 days.

(21) Appl. No.: 14/759,670

(22) PCT Filed: Jan. 16, 2014

(86) PCT No.: PCT/JP2014/000170
§ 371 (c)(1),
(2) Date: Jul. 8, 2015

(87) PCT Pub. No.: WO2014/112373
PCT Pub. Date: Jul. 24, 2014

(65) Prior Publication Data
US 2015/0346089 A1 Dec. 3, 2015

(30) Foreign Application Priority Data
Jan. 21, 2013 (JP) .................... 2013-8643

(51) Int. Cl.
*G02B 6/42* (2006.01)
*G01N 15/06* (2006.01)
(Continued)

(52) U.S. Cl.
CPC ............ *G01N 21/43* (2013.01); *B60S 1/0833* (2013.01); *G01N 2021/435* (2013.01); *G01N 2201/062* (2013.01)

(58) Field of Classification Search
CPC .................... B60S 1/0833; G01N 2021/435
(Continued)

(56) References Cited

U.S. PATENT DOCUMENTS
5,581,240 A 12/1996 Egger
5,801,539 A 9/1998 Schroder
(Continued)

FOREIGN PATENT DOCUMENTS
JP 61-172033 A 8/1986
JP 09-257952 A 10/1997
(Continued)

OTHER PUBLICATIONS

International Search Report and Written Opinion of the International Searching Authority dated Mar. 25, 2014 issued in the corresponding International application No. PCT/JP2014/000170 (and English translation).

*Primary Examiner* — Thanh Luu
(74) *Attorney, Agent, or Firm* — Posz Law Group, PLC (57) ABSTRACT

An adhering matter determination portion includes an irradiation portion, a light receiving portion and a determination portion. The irradiation portion radiates a light to a plurality of different areas of a transparent plate. The light receiving portion converts reflected waves reflected at the different areas into electrical signals. The determination portion compares at least one of detection signals outputted from the light receiving portion with a determination threshold. When the detection signal is lower than the determination threshold, the determination portion determines that there is an adhering matter on the transparent plate. The determination portion compares the detection signals. When a difference of the detection signals is higher than a condensation determination value, the determination portion determines that the adhering matter is raindrops. When the difference of the detection signals is lower than the condensation determina-
(Continued)

tion value, the determination portion determines that the adhering matter is dewdrops.

10 Claims, 5 Drawing Sheets

(51) Int. Cl.
  *G01N 21/43* (2006.01)
  *B60S 1/08* (2006.01)
(58) Field of Classification Search
  USPC .................................. 250/227.25, 573–575
  See application file for complete search history.

(56) References Cited

U.S. PATENT DOCUMENTS

| | | |
|---|---|---|
| 6,307,198 B1 | 10/2001 | Asakura et al. |
| 6,376,824 B1 | 4/2002 | Michenfelder et al. |
| 2003/0069674 A1 | 4/2003 | Stam et al. |
| 2005/0285557 A1 | 12/2005 | Morishita |
| 2006/0207325 A1 | 9/2006 | Kataoka et al. |
| 2007/0272884 A1* | 11/2007 | Utida .................... B60S 1/0822 250/573 |
| 2010/0299025 A1 | 11/2010 | Oishi et al. |

FOREIGN PATENT DOCUMENTS

| | | |
|---|---|---|
| JP | 10-119729 A | 5/1998 |
| JP | 2004-257976 A | 9/2004 |
| JP | 2007-033153 A | 2/2007 |
| JP | 2011-168090 A | 9/2011 |
| JP | 2011-252856 A | 12/2011 |

* cited by examiner

ADHERING MATTER DETERMINATION DEVICE

CROSS REFERENCE TO RELATED APPLICATION

This application is a U.S. national stage of International Application No. PCT/JP2014/000170 filed on Jan. 16, 2014 and is based on Japanese Patent Application No. 2013-8643 filed on Jan. 21, 2013, the disclosures of which are incorporated herein by reference.

TECHNICAL FIELD

The present disclosure relates to an adhering matter determination device that determines an adhering matter adhering to a transparent plate.

BACKGROUND ART

A raindrop detector that detects the quantity of waterdrops adhering to a window glass has been known, for example, as indicated by patent literature 1. The raindrop detector includes a waterdrop detecting portion that detects the quantity of waterdrops adhering to the window glass at a predetermined interval, and a change rate calculating portion that calculates the rate of change of the quantity of the waterdrops in each predetermined interval detected by the waterdrops detecting portion. The raindrop detector further includes a determining portion that determines an adhering state of waterdrops to the window glass based on the rate of change of the quantity of the waterdrops calculated. When the rate of change of the quantity of waterdrops is equal to or greater than a predetermined rate of increase, the determining portion determines that the window glass is in a condensed state in which the waterdrops adhering to the window glass are condensed on the window glass.

PRIOR ART LITERATURE

Patent Literature

Patent Literature 1: JP 2011-168090 A

SUMMARY OF INVENTION

As described above, the raindrop detector of the patent literature 1 determines that the window glass is in the condensed state when the rate of change of the quantity of the waterdrops is equal to or greater than the predetermined rate of increase. However, even when the rate of change of the quantity of the waterdrops is lower than the predetermined rate of increase, the condensation will occur depending on the temperature inside of a vehicle, the temperature outside of the vehicle, and the humidity outside of the vehicle. Therefore, in the raindrop detector of the patent literature 1, there is a possibility that the determination whether dewdrops adhere to the window glass cannot be made.

The present disclosure is made in view of the above issue, and it is an object of the present disclosure to provide an adhering matter determination device with an enhanced determination accuracy of adherence of dewdrops.

According to an aspect of the present disclosure, an adhering matter determination device includes an irradiation portion, a light receiving portion, and a determination portion. The irradiation portion emits light to a plurality of different areas of an inner surface of a transparent plate. The light receiving portion converts reflected waves of the light emitted from the irradiation portion and reflected at the different areas into electrical signals, and outputs the electrical signals to the determination portion as detection signals. The determination portion compares at least one of the detection signals outputted from the light receiving portion with a determination threshold. When the detection signal is lower than the determination threshold, the determination portion determines that there is an adhering matter on the transparent plate. The determination portion compares the plurality of detection signals corresponding to the reflected waves reflected at the plurality of different areas. When a difference between the plurality of detection signals is higher than a condensation determination value, the determination portion determines that the adhering matter is raindrops. When the difference between the plurality of detection signals is lower than the condensation determination value, the determination portion determines that the adhering matter is dewdrops.

When the raindrops or the dewdrops adhere to the transparent plate, a part of the light radiated to the transparent plate transmits through the transparent plate and the adhering matter to the outside. Therefore, the amount of the reflected waves reflected by the transparent plate reduces, and the amount of the reflected waves entering the light receiving portion reduces. As a result, the detection signals are lowered. Therefore, when the detection signal outputted from the light receiving portion is lower than the determination threshold, the determination portion determines that there is an adhering matter on the transparent plate.

When it is raining, raindrops randomly adhere to the outer surface of the transparent plate. Therefore, the light quantity of the reflected waves is different between the different areas. As a result, the intensity (voltage level) of the plurality of detection signals is different. Therefore, when the difference between the plurality of detection signals (hereinafter simply referred to as a difference value) corresponding to the reflected waves reflected at the different areas is higher than the condensation determination value, the determination portion determines that the adhering matter is the raindrops On the other hand, when condensation occurs on the outer surface of the transparent plate, dewdrops evenly adheres to the outer surface of the transparent plate. In this case, the light quantity of the reflected waves is the same between the different areas. Therefore, the detection signals have the same voltage level. As a result, when the difference value is lower than the condensation determination value, the determination portion determines that the adhering matter is the dewdrops.

As described above, the presence of the dewdrops is directly detected by comparing the reflected waves reflected at the different areas. Accordingly, as compared with an indirect detection where the presence of the dewdrops is detected based on the rate of increase of the reflected waves, the accuracy of determining the adherence of dewdrops enhances.

According to a second aspect of the present disclosure, in the adhering matter determination device according to the first aspect, when the difference of the plurality of detection signals is higher than the condensation determination value and the intensity of the detection signal randomly changes during a first predetermined period, the determination portion determines that the adhering matter is the raindrops. When the difference of the plurality of detection signals is lower than the condensation determination value and the intensity of the detection signal reduces continuously at several times at an interval shorter than that the raindrops adhere to the transparent plate in a second predetermined period, the determination portion determines that the adhering matter is the dewdrops.

As described above, when it is raining, the raindrops randomly adhere to the outer surface of the transparent plate. When the raindrops pour down on the transparent plate, the raindrops combine with each other and flow down from the transparent plate due to the own weight. Therefore, the light quantity of the reflected waves reflected on the transparent plate randomly changes. As a result, the intensity of the detection signal randomly changes. Accordingly, when the voltage level of the detection signal randomly changes in the first predetermined period, the determination portion determines that the adhering matter is the raindrops.

When the condensation occurs on the outer surface of the transparent plate, the dewdrops evenly adhere to the outer surface of the transparent plate. When the condensation progresses, the quantity of the dewdrops adhering to the outer surface of the transparent plate increases. Therefore, the light quantity of the reflected waves reflected on the transparent plate continuously reduces. As a result, the voltage level of the detection signal continuously reduces. Accordingly, when the voltage level of the detection signal continuously reduces in the second predetermined period, the determination portion determines that the adhering matter is the dewdrops.

As described above, the adhering matter is determined either the raindrops or the dewdrops based on not only the difference value but also the behavior of the voltage level of the detection signal. Accordingly, the accuracy of determination of the adherence of dewdrops improves, as compared with the structure where the raindrops or the dewdrops are determined based on the difference value.

BRIEF DESCRIPTION OF DRAWINGS

The above and other objects, features and advantages of the present disclosure will become more apparent from the following detailed description made with reference to the accompanying drawings, in which:

FIG. 4 is a graph illustrating an expected signal, a detection signal when dewdrops adhere to, and a detection signal when raindrops adhere to;

DESCRIPTION OF EMBODIMENTS

Hereinafter, an embodiment of an adhering matter determination device of the present disclosure will be described with reference to the drawings.

First Embodiment

An adhering matter determination device 100 according to the present embodiment will be described with reference to FIGS. 1 to 5. The adhering matter determination device 100 determines an adhering matter adhering to an outer surface of a windshield WS. In a case of being installed in a vehicle, the adhering matter determination device 100 outputs a determination signal of an adhering matter to a wiper control part (not shown) of the vehicle, thereby to remove the adhering matter adhering to the windshield WS. The windshield WS corresponds to a transparent plate.

Figure 1:
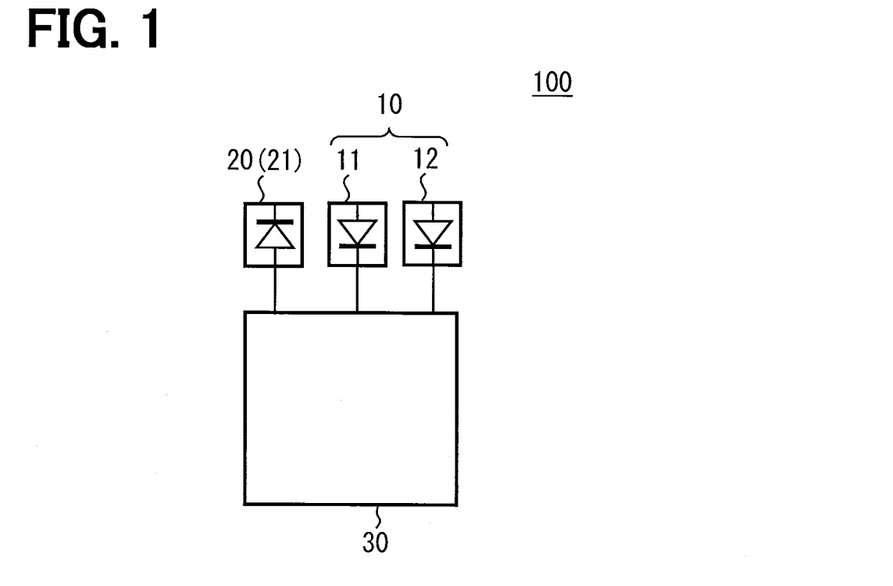
FIG. 1 is a block diagram illustrating a schematic structure of an adhering matter determination device.
Figure 2:
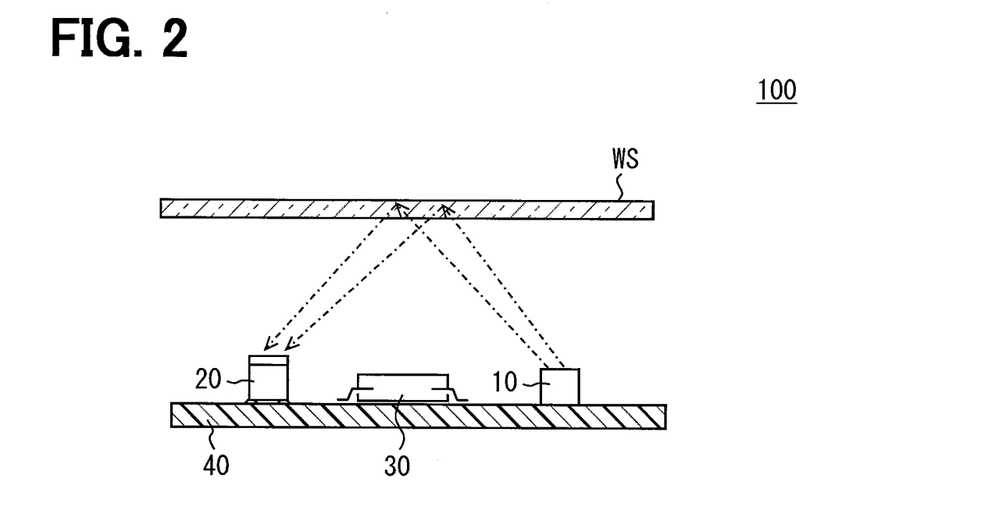
FIG. 2 is a cross-sectional view illustrating an arrangement relationship between the adhering matter determination device and a windshield.

As shown in FIG. 1 and FIG. 2, the adhering matter determination device 100 includes an irradiation portion 10, a light receiving portion 20, and a determination portion 30, as main components. The light emitted from the irradiation portion 10 is reflected on the windshield WS, and the light reflected is incident on the light receiving portion 20. The light receiving portion 20 converts the light received into an electrical signal, and outputs the electrical signal converted to the determination portion 30. The determination portion 30 determines an adhering matter (raindrops and dewdrops) adhering to the windshield WS based on the output signal of the light receiving portion 20. In the present embodiment, as shown in FIG. 2, the main components 10 to 30 described above are mounted on one substrate 40. The substrate 40 is spaced from the inner surface of the windshield WS by a predetermined distance.

Figure 3:
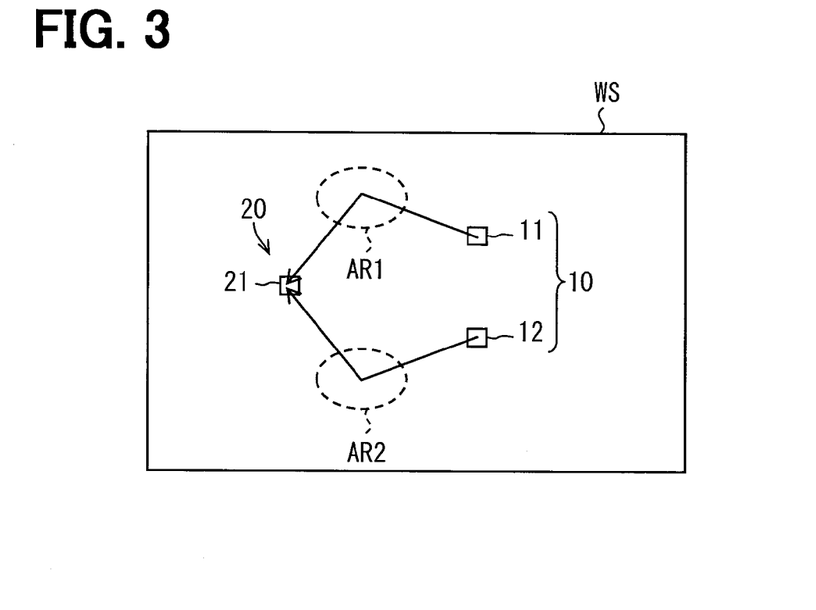
FIG. 3 is a schematic view illustrating a relationship between PD and LED.

The irradiation portion 10 emits the light to the inner surface of the windshield WS. The irradiation portion 10 of the present embodiment includes a plurality of LEDs 11 and 12. The LEDs 11 and 12 emit light to different areas (areas AR1 and AR2 encircled by dashed lines) of the windshield WS, as shown in FIG. 3.

The LEDs 11 and 12 are intermittently driven by pulse drive currents supplied from the determination portion 30. The duty ratio of the drive currents is lower than 50%. The LEDs 11 and 12 are alternately driven. When one of the LEDs 11 and 12 emits light, the other of the LEDs 11 and 12 does not emit light. The LEDs 11 and 12 alternately emit the light.

Figure 4:
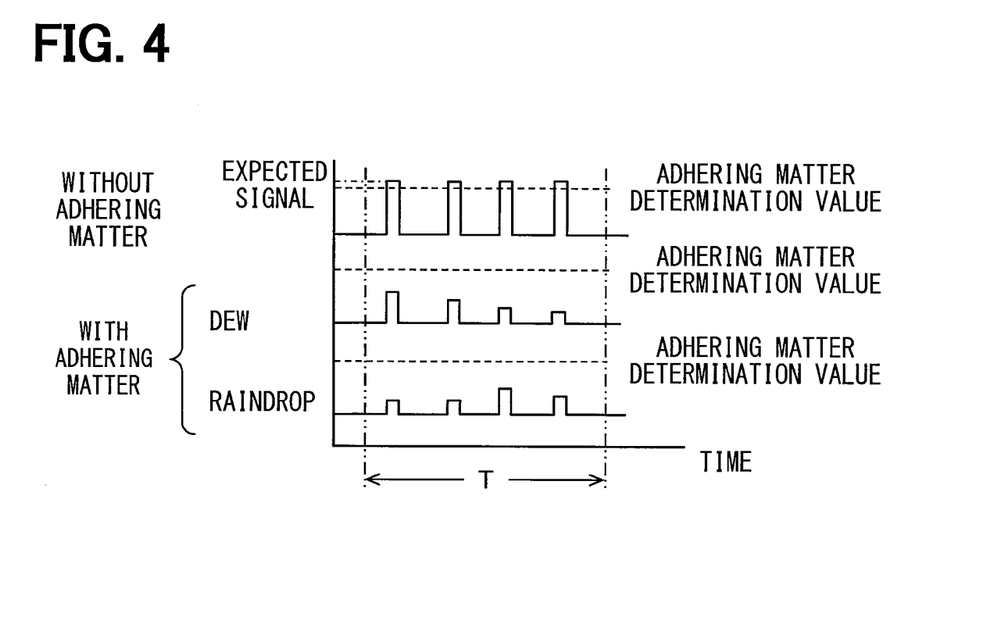

The light receiving portion 20 receives a reflected wave of the light that is emitted from the irradiation portion 10 and reflected on the windshield WS, and converts the reflected wave into the electrical signal. The light receiving portion 20 according to the present embodiment has one PD 21 (photo detector). The LEDs 11 and 12 are provided for the PD 21. As described above, the LEDs 11 and 12 are intermittently driven by the pulse drive currents supplied from the determination portion 30. Therefore, as shown in FIG. 4, the PD 21 outputs the output signal (hereinafter also referred to as the detection signal) intermittently. The detection signal, which is outputted intermittently, is inputted to the determination portion 30.

The LEDs 11 and 12 emit light to different areas AR1 and AR2, as described above. Further, the LEDs 11 and 12 alternately emit the light. Therefore, the PD 21 receives the reflected waves reflected at the different areas AR1 and AR2 alternately. The determination portion 30 receives a plurality of detection signals corresponding to the plurality of reflected waves reflected at the different areas AR1 and AR2.

The determination portion 30 determines a material adhering to the outer surface of the windshield WS based on the detection signals. The determination portion 30 has: an expected signal (see FIG. 4) that is expected to be outputted from the PD 21 when there is no adhering matter on the windshield WS; an adhering matter determination value having a voltage value lower than the expected signal; and a condensation determination value having a voltage value lower than the adhering matter determination value. The determination portion 30 according to the present embodiment compares the detection signal with the adhering matter determination value. When the intensity (voltage level) of the detection signal is lower than the adhering matter determination value, the determination portion 30 determines that there is a material (raindrops or dewdrops) adhering to the windshield WS. The determination portion 30 further determines a difference (hereinafter referred to as a difference value) between the plurality of detection signals corresponding to the reflected waves reflected at the different areas AR1 and AR2 with a condensation determination value, thereby to determine whether the adhering matter is raindrops or dewdrops. The adhering matter determination value is a value equal to or higher than 90% and less than 100% of the voltage level of the expected signal. The condensation determination value is lower than the adhering matter determination value. In the present embodiment, the adhering matter determination value corresponds to a determination threshold.

When there is the adhering matter, such as raindrops and dewdrops, on the windshield WS, a part of the light emitted from the irradiation portion 10 to the windshield WS transmits through the windshield WS and the adhering matter to the outside. Therefore, the reflection wave reflected by the windshield WS is reduced, and the reflection wave incident on the light receiving portion 20 is reduced. As a result, the detection signal is lowered. As such, when the detection signal is lower than the adhering matter determination value, the determination portion 30 determines that there is the adhering matter on the windshield WS.

When it is raining, the raindrops randomly adhere to the outer surface of the windshield WS. Therefore, the light quantities of the reflected waves reflected at the different areas AR1 and AR2 are different. As a result, the detection signals have different voltage levels. Therefore, when the difference value is higher than the condensation determination value, the determination portion 30 determines that the adhering matter is the raindrops.

On the other hand, when the condensation occurs on the outer surface of the windshield WS, dewdrops evenly adhere to the outer surface of the windshield WS. Therefore, the light quantities of the reflected waves reflected at the different areas are the same. As a result, the detection signals have the same voltage level. Accordingly, when the difference value is lower than the condensation determination value, the determination portion determines that the adhering matter is the dewdrops.

As described above, when it is raining, the raindrops randomly adhere to the outer surface of the windshield WS. When the raindrops pour on the windshield WS, the raindrops combine with each other and flow down from the windshield WS due to the own weight. Therefore, the light quantity of the reflected waves reflected on the windshield WS randomly changes. As a result, the voltage level of the detection signal randomly changes, as shown in FIG. 4. As such, when the difference value is higher than the condensation determination value and the voltage level of the detection signal randomly changes during a first predetermined period, the determination portion determines that the adhering matter is the raindrops.

When the condensation occurs on the outer surface of the windshield WS, the dewdrops evenly adhere to the outer surface of the windshield WS. When the condensation progresses, the quantity of dewdrops adhering to the outer surface of the windshield WS increases. Therefore, the light quantity the reflected waves reflected on the windshield WS continuously reduces. As a result, the voltage level of the detection signal continuously reduces, as shown in FIG. 4.

As such, when the difference value is lower than the condensation determination value and the voltage level of the detection signal continuously reduces in a second predetermined period, the determination portion 30 determines that the adhering matter is the dewdrops.

In the present embodiment, the first predetermined period and the second predetermined period have the same time length. In the description hereinafter, the first predetermined period and the second predetermined period are both simply referred to as a predetermined period T. The predetermined period T is shown in FIG. 4.

When determining that the adhering matter is the dewdrops, the determination portion 30 lowers the voltage level of the adhering matter determination value. The determination portion 30 determines the detection signal with the adhering matter determination value the voltage level of which has been lowered, to determine the raindrops. Thereafter, the determination portion 30 returns the voltage level of the adhering matter determination value to the original voltage level.

Figure 5:
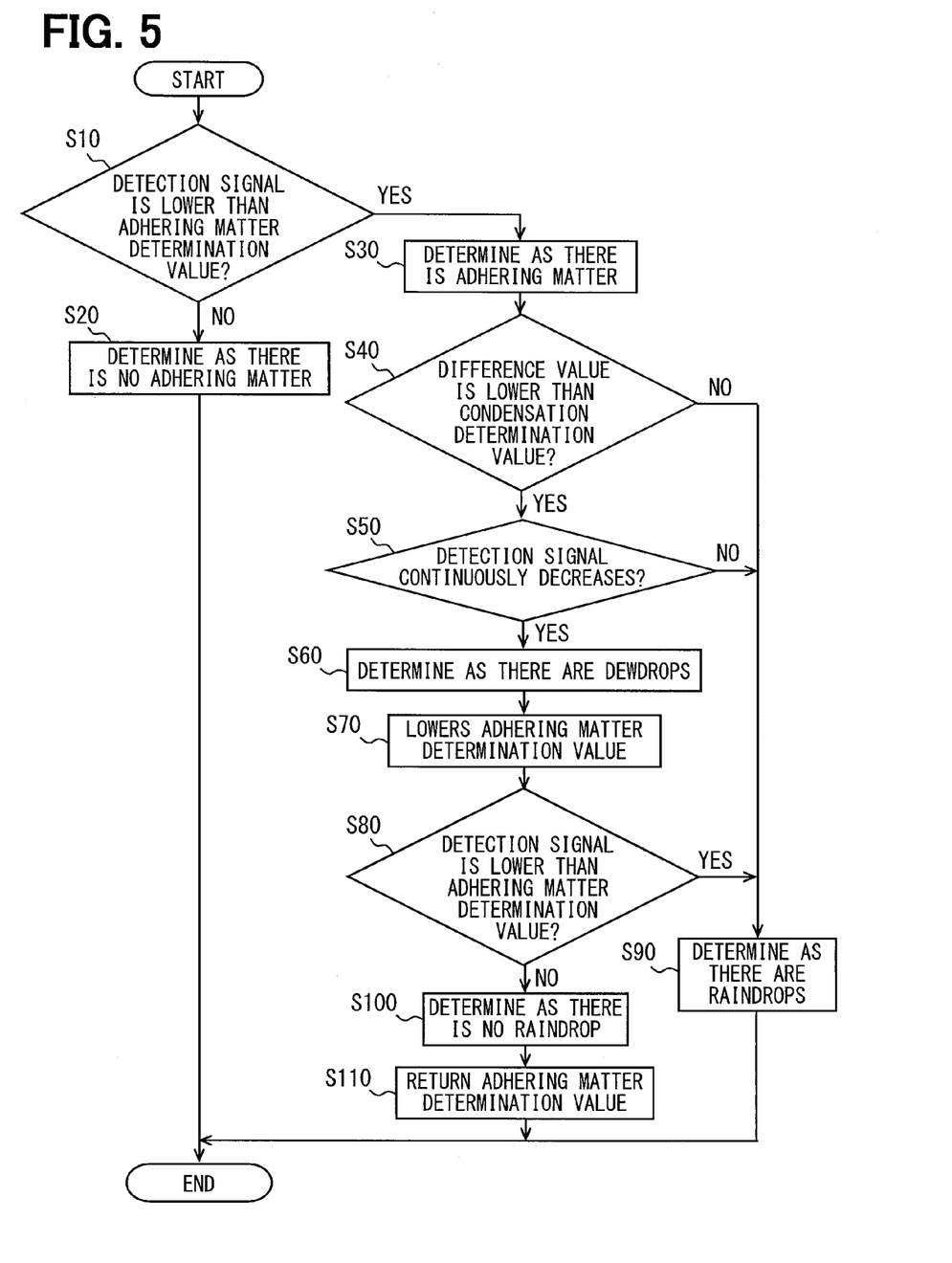
FIG. 5 is a flowchart for explaining a determination of an adhering matter.

Next, the determination of the adhering matter performed by the determination portion 30 will be described with reference to FIG. 4 and FIG. 5. First, the determination portion 30 acquires the detection signal of the PD 21. At S10, the determination portion 30 determines whether the detection signal is lower than the adhering matter determination value. When determining that the detection signal is not lower than the adhering matter determination value, the determination portion 30 determines that there is no adhering material on the windshield WS at S20 and ends the adhering matter determination. On the other hand, when determining that the detection signal is lower than the adhering matter determination value at S10, the determination portion 30 determines that there is the adhering matter on the windshield WS at S30, and proceeds to S40.

At S40, the determination portion 30 calculates the difference value between the plurality of detection signals corresponding to the plurality of reflected waves reflected at the different areas AR1 and AR2. The determination portion 30 determines whether the difference value is lower than the condensation determination value. When determining that the difference value is not lower than the condensation determination value, the determination portion 30 determines that there is the raindrops on the windshield WS at S90, and then ends the adhering matter determination. On the other hand, when determining that the difference value is lower than the condensation determination value at S40, the determination portion 30 proceeds to S50.

At S50, the determination portion 30 determines whether the detection signal continuously decreases in the predetermined period T. When determining that the detection signal does not continuously decrease, the determination portion 30 determines that there is the raindrops on the windshield S90, and ends the adhering matter determination. On the other hand, when determining that the detection signal continuously changes at S50, the determination portion 30 determines that there is the dewdrops on the windshield (the condensation has occurred on the windshield WS) at S60, and proceeds to S70. In this case, the continuous change means a situation that, when the raindrops continuously adhere to the windshield WS, the detection signal changes at an interval shorter than the interval where the raindrops adhere and several times continuously. An example is that the decrease equal to or greater than 1 LSB is detected continuously over 16 times every 5 ms. Such a determination restricts erroneous determination when the number of times of continuous change is excessively low or when the interval where the detection signal changes is excessively short.

At S70, the determination portion 30 lowers the voltage level of the adhering matter determination value, and then proceeds to S80.

At S80, the determination portion 30 determines whether the detection signal is lower than the adhering matter determination value the voltage level of which has been lowered at S70. When determining that the detection signal is lower than the adhering matter determination value at S80, the determination portion 30 determines that there is the raindrops on the windshield at S90, and then ends the adhering matter determination. On the other hand, when determining that the detection signal is not lower than the adhering matter determination value at S80, the determination portion 30 determines that there is no raindrops on the windshield WS (it is not raining) at S100, and then proceeds to S110.

At S110, the determination portion 30 returns the voltage level of the adhering matter determination value, which has been lowered at S70, to the original value, and ends the adhering matter determination. The determination portion 30 performs the S10 through S110 in a loop. Thus, the determination portion 30 repeats the determination of the adhering matter.

When determining that there are the raindrops on the windshield WS, the determination portion 30 outputs the determination signal to an external device. In the case where the adhering matter determining device 100 is installed in the vehicle, the determination signal described above is provided to a wiper control unit (not shown) of the vehicle to drive the wiper. Thus, the raindrops adhering on the windshield WS is removed.

Likewise, when determining that there are the dewdrops on the windshield WS, the determination portion 30 outputs the determination signal to an external device. In the case where the adhering matter determining device 100 is installed in the vehicle, the determination signal described above is provided to a temperature control unit (not shown) of the vehicle to rise the temperature of air blown to the windshield WS. Thus, the dewdrops adhering on the windshield WS is removed.

Next, effects of the adhering matter removing device 100 according to the present embodiment will be described. As described above, when there is the adhering matter, such as the raindrops or the dewdrops, on the windshield WS, the detection signal is lowered. For this reason, when the detection signal is lower than the adhering matter determination value (expected signal), the determination portion 30 determines that there is the adhering matter on the windshield WS. When it is raining, the detection signals corresponding to the reflected waves reflected at the different areas AR1 and AR2 have different voltage levels. For this reason, when the difference (difference value) of the detection signals is higher than the condensation determination value, the determination portion 30 determines that the adhering matter is the raindrops. On the other hand, when the condensation has occurred on the outer surface of the windshield WS, the detection signals have the same voltage level. For this reason, when the difference value is lower than the condensation determination value, the determination portion 30 determines that the adhering matter is the dewdrops.

The adhering matter determination device 100 directly detects the presence of the dewdrops by comparing the reflected waves reflected at the different areas AR1 and AR2. Therefore, the accuracy of determining the adherence of the dewdrops enhances, as compared with the structure in which the presence of the dewdrops is indirectly detected based on the rate of increase of the reflected waves. This is the main effect achieved by the adhering matter determination device 100.

As described above, when it is raining, the voltage level of the detection signal randomly changes. When the condensation has occurred on the outer surface of the windshield WS, the voltage level of the detection signal continuously lowers. On the other hand, when the difference value is higher than the condensation determination value and the voltage level of the detection signal randomly changes in the predetermined period T, the determination portion 30 determines that the adhering matter is the raindrops. When the difference value is lower than the condensation determination value and the voltage level of the detection signal continuously lowered in the predetermined period T, the determination portion 30 determines that the adhering matter is the dewdrops. In this way, the determination portion 30 determines the raindrops and the dewdrops based on not only the difference value but also the behavior of the voltage level of the detection signal. Therefore, the determination accuracy of the adherence of the dewdrops enhances, as compared with the structure in which the raindrops and the dewdrops are determined based on the difference value only.

The determination portion 30 determines the presence of the adhering matter when the voltage level of the detection signal is lower than the adhering matter determination value. It is not always true that the outer surface and the inner surface of the windshield WS are clean. Therefore, it is assumed that the detection signal is lower than the expected signal, also in the case where there are no raindrops and dewdrops on the outer surface of the windshield WS. Therefore, in the case where the presence or absence of the adhering matter is determined based on the expected signal and the detection signal, there is a possibility that the determination portion 30 will erroneously determine. To restrict such an erroneous determination, the adhering matter determination value that has the voltage level lower than that of the expected signal is provided, in place of the expected signal. The adhering matter is determined when the voltage level of the detection signal is lower than the adhering matter determination value. As such, the erroneous determination of the determination portion 30 reduces.

When determining that there are the dewdrops on the windshield WS, the determination portion 30 lowers the voltage level of the adhering matter determination value. When there are the dewdrops on the windshield WS, the detection signal is lower than the adhering matter determination value (expected signal). For this reason, there is a possibility that the determination portion 30 determines that it is raining, although it is not raining. As described above, therefore, when there are the dewdrops on the windshield WS, the voltage level of the adhering matter determination value is lowered. Accordingly, it is less likely that the adherence of the raindrops to the windshield WS will be erroneously determined, when it is not raining.

The determination portion 30 determines whether there are the raindrops on the windshield WS by comparing the detection signal with the adhering matter determination value the voltage of which has been lowered. When there are the dewdrops on the windshield WS and it is raining, the voltage level of the detection signal is lowered due to the dewdrops and the raindrops. Therefore, the amount of decrease does not depend on only the raindrops. In order to consider the decrease in the voltage drop of the detection signal due to the dewdrops, the voltage level of the adhering matter determination value, which is to be compared with the detection signal, is lowered. In this case, the difference between the detection signal and the adhering matter determination value is reduced, and the deterioration of detection accuracy of the raindrops is restricted.

After comparing the detection signal with the adhering matter determination value the voltage level of which has been lowered, the determination portion 30 returns the voltage level of the adhering matter determination value to the original voltage level. The quantity of the adhering matter adhering to the windshield WS varies with time. Therefore, it is preferable that the voltage level of the adhering matter determination value is returned to the original voltage level every time the detection signal is compared with the adhering matter determination value, and then the voltage of the adhering matter determination value is adjusted again. In such a case, the adhering matter determination value is adjusted to the value according to the quantity of the adhering matter actually adhering to the windshield WS.

The preferred embodiment of the present disclosure has been described hereinabove. However, the present disclosure is not limited to the embodiment described hereinabove, but may be implemented in various other ways without departing from the gist of the present disclosure.

Figure 6:
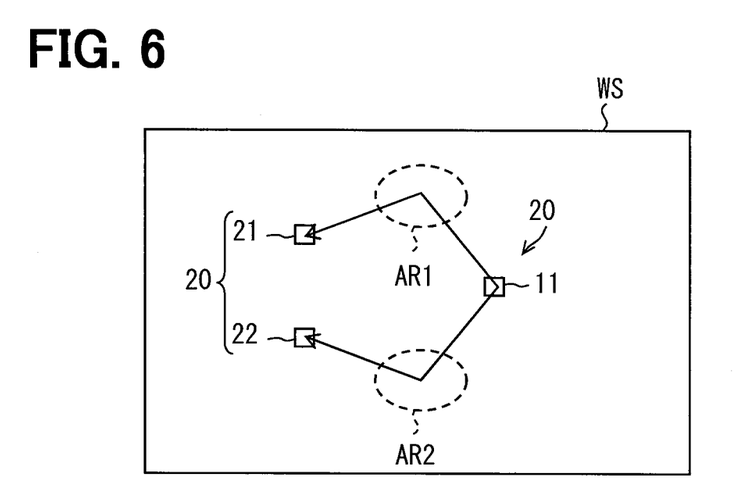
FIG. 6 is a schematic diagram illustrating a modification of the relationship between the PD and the LED.

In the embodiment, it is exemplified that the irradiation portion 10 has the LEDs 11 and 12, the light receiving portion 20 has one PD 21, and the LEDs 11 and 12 provided for the PD 21. However, the number of the LEDs and the number of the PD may not be limited to the example described above as long as the reflection lights reflected at different areas can be received by the PD. For example, as shown in FIG. 6, a structure in which the irradiation portion 10 has one LED 11, the light receiving portion 20 has two PDs 21 and 22, and the LED11 is provided for the PDs 21 and 22 may be employed. Since the light emitted from the LED 11 radiates, the light is applied to the areas AR1 and AR2. The reflected light reflected at the AR1 is incident on the PD21, and the reflected light reflected at the AR2, which is different from the area AR1, is incident on the PD 22.

Figure 7:
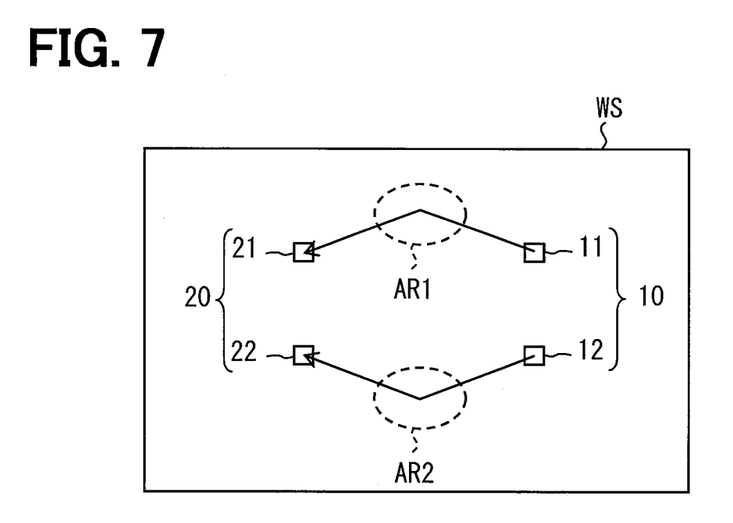
FIG. 7 is a schematic diagram illustrating a modification of the relationship between the PD and the LED.

For example, as shown in FIG. 7, a structure in which the irradiation portion 10 has two LEDs 11 and 12, the light receiving portion 20 has two PDs 21 and 22, the LED 11 is provided to correspond to the PD 21 and the LED 12 is provided to correspond to the PD 22 may be employed.

In the embodiment, it is exemplified that the reflected lights reflected at two different areas AR1 and AR2 are incident on the light receiving portion 20. However, the number of areas is not limited to the example described above as long as there is plural number of areas.

In the embodiment, it is exemplified that the determination portion 30 determines that there is the adhering matter when the voltage level of the detection signal is lower than the adhering matter determination value. Alternatively, the expected signal may be used, in place of the adhering matter determination value, and a structure in which the presence of the adhering mater is determined when the voltage level of the detection signal is lower than the expected signal may be employed. Also in such a structure, the advantageous effects described hereinabove will be achieved. In other words, in the example of FIG. 5, the detection signal is compared with the adhering matter determination value as the determination threshold in the determination of S10. Alternatively, the expected signal value may be employed as the determination threshold, and the presence of the adhering matter may be determined by comparing the detection signal with the expected signal value. In the case where the presence of the adhering matter is determined by comparing the detection signal with the determination threshold, at least one detection signal may be compared with the determination threshold.

In the embodiment, it is exemplified that the determination portion 30 determines that the adhering matter is the raindrops when the difference value is higher than the condensation determination value and the voltage level of the detection signal randomly changes in the predetermined period T. Alternatively, the determination portion 30 may determine that the adhering mater is the raindrops when the difference value is higher than the condensation determination value. In the embodiment, it is exemplified that the determination portion 30 determines that the adhering matter is the dewdrops when the difference value is lower than the condensation determination value and the voltage level of the detection signal continuously decreases in the predetermined period T. Alternatively the determination portion 30 may determine that the adhering matter is the dewdrops when the difference value is lower than the condensation determination value. In this case, S50 shown in FIG. 5 is omitted.

Figure 8:
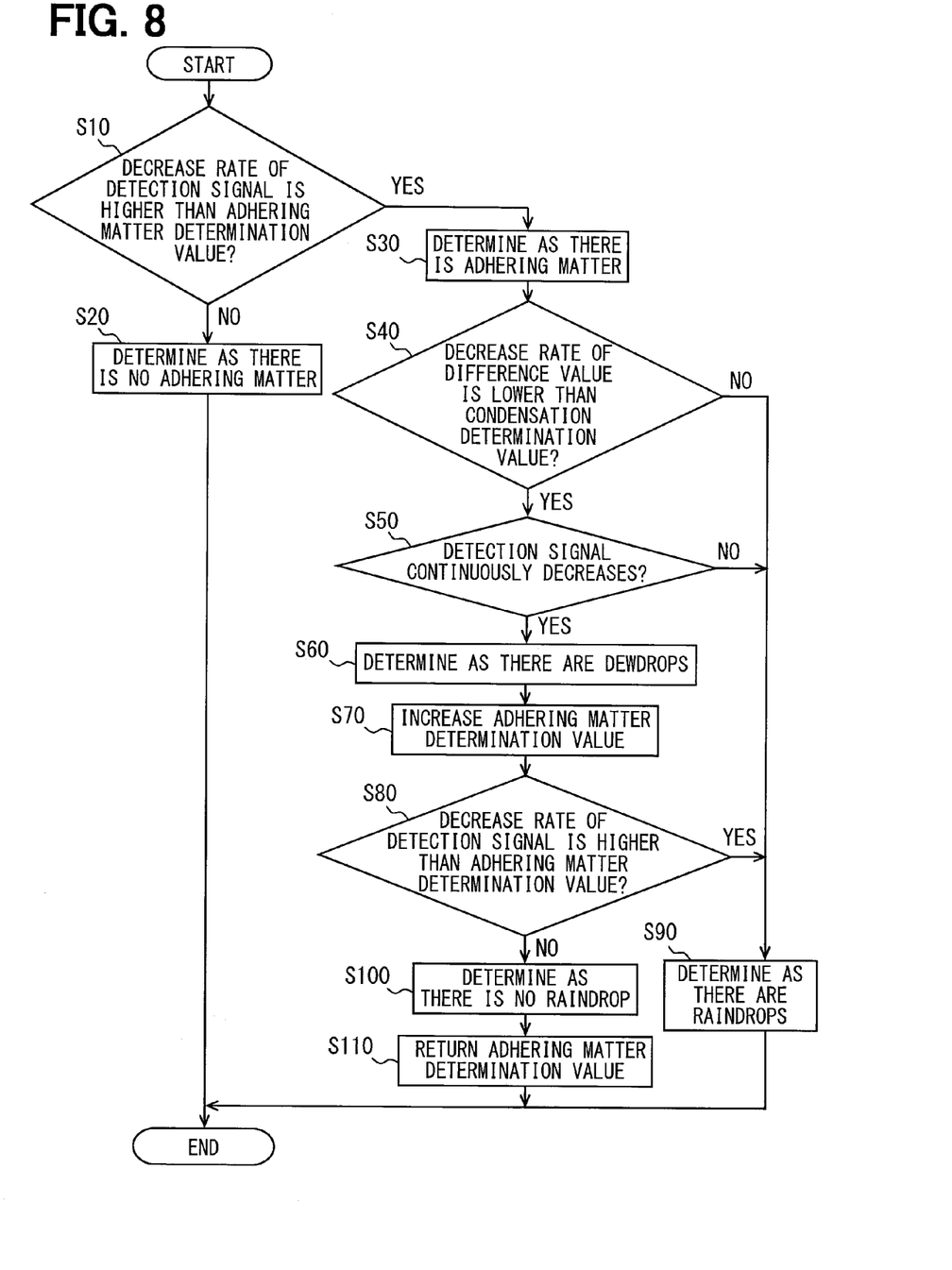
FIG. 8 is a flowchart for explaining a modification of the determination of the adhering matter.

In the embodiment, it is exemplified that the determination portion 30 determines whether there is the adhering matter (raindrops and dewdrops) on the windshield WS by comparing the voltage level of the detection signal with the adhering matter determination value at S10. Also, it is exemplified that the determination portion 30 determines whether there is the raindrops on the windshield WS by comparing the voltage level of the detection signal with the adhering matter determination value at S80. Alternatively, the determination portion 30 may determine whether there is an adhering matter or raindrops on the windshield WS based on the rate of decrease of the voltage level of the detection signal. In such a case, as shown in FIG. 8, the determination portion 30 determines whether the rate of decrease of the detection signal is greater than an adhering mater determination value at S10. When the rate of decrease of the detection signal is greater than the adhering mater determination value, the determination portion 30 determines that there is an adhering matter on the windshield WS. At S80, the determination portion 30 determines whether the rate of decrease of the detection signal is greater than the adhering matter determination value. When the rate of decrease of the detection signal is greater than the adhering matter determination value, the determination portion 30 determines that there is the raindrops on the windshield WS. In the case of this modification, the adhering matter determination value does not indicate the voltage level, but indicates a rate of decrease of the voltage level. Also in the case where the expected signal value is used as the determination threshold, it indicates the rate of decrease of the voltage level. The value may be arbitrary set according to the sensitivity intended by a user. At S70, the value of the adhering mater determination value is increased.

Furthermore, as shown in FIG. 8, it may possible to employ a structure in which the determination portion 30 determines whether the rate of decrease of the voltage level of the difference value is lower than the condensation determination value, in place of the voltage level of the difference value, at S40. In this case, similarly to the adhering matter determination value, the condensation determination value indicates the rate of decrease of the voltage level, in place of the voltage level.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

The invention claimed is:

1. An adhering matter determination device comprising:
an irradiation portion radiating a light toward a plurality of different areas of an inner surface of a transparent plate;
a light receiving portion converting a plurality of reflection waves of the light radiated from the radiation portion and reflected at the plurality of different areas into a plurality of electrical signals and outputting the electrical signals as a plurality of detection signals; and
a determination portion determining an adhering matter adhering to an outer surface of the transparent plate based on the plurality of detection signals outputted from the light receiving portion, wherein
the determination portion compares at least one of the plurality of detection signals outputted from the light receiving portion with a determination threshold, and determines that there is the adhering matter on the transparent plate when the at least one of the plurality of detection signals is lower than the determination threshold, and
the determination portion compares the plurality of detection signals, determines that the adhering matter is raindrops when a difference of the plurality of detection signals is higher than a condensation determination value, and determines that the adhering matter is dewdrops when the difference of the plurality of detection signals is lower than the condensation determination value.

2. The adhering matter determination device according to claim 1, wherein
the determination portion determines that the adhering matter is the raindrops when the difference of the plurality of detection signals is higher than the condensation determination value and an intensity of the at least one of the plurality of the detection signals randomly changes in a first predetermined period, and
the determination portion determines that the adhering mater is the dewdrops when the difference of the plurality of detection signals is lower than the condensation determination value, and the intensity of the at least one of the plurality of the detection signals continuously lowers several times at an interval shorter than an interval that the raindrops adhere to the transparent plate in a second predetermined period.

3. The adhering matter determination device according to claim 1, wherein
the determination threshold has an expected signal value that is a value expected to be outputted from the light receiving portion when there is no adhering matter on the transparent plate.

4. The adhering matter determination device according to claim 1, wherein
the determination threshold is an adhering matter determination value that is lower than an expected signal value expected to be outputted from the light receiving portion when there is no adhering matter on the transparent plate.

5. The adhering matter determination device according to claim 4, wherein
when the determination portion determines that there are the dewdrops on the transparent plate, the determination portion lowers the adhering matter determination value.

6. The adhering matter determination device according to claim 5, wherein
the determination portion determines whether there are the raindrops on the transparent plate by comparing the at least one of the plurality of detection signals with the adhering matter determination value lowered.

7. The adhering matter determination device according to claim 6, wherein
the determination portion returns the adhering matter determination value lowered to an original value, after comparing the at least one of the plurality of detection signals with the adhering mater determination value lowered.

8. The adhering matter determination device according to claim 1, wherein
the irradiation portion includes a plurality of LEDs that are alternately driven, and
the plurality of LEDs radiates the light to the different areas.

9. The adhering mater determination device according to claim 1, wherein
the light receiving portion includes a plurality of PDs,
the plurality of PDs is disposed to respectively receive the plurality of reflected waves radiated to and reflected at the plurality of different areas.

10. The adhering matter determination device according to claim 1, wherein
the condensation determination value is lower than the determination threshold.

* * * * *